(12) United States Patent
Schmidt et al.

(10) Patent No.: US 11,912,969 B2
(45) Date of Patent: Feb. 27, 2024

(54) TRANSPARENT SPECIMEN SLIDE

(71) Applicant: HELMHOLTZ-ZENTRUM DRESDEN - ROSSENDORF E.V., Dresden (DE)

(72) Inventors: Heidemarie Schmidt, Dresden (DE); Ilona Skorupa, Dresden (DE); Katarzyna Wiesenhütter, Dresden (DE); Lars Rebohle, Coswig (DE)

(73) Assignee: HELMHOLTZ-ZENTRUM DRESDEN—ROSSENDORF E.V., Dresden (DE)

( * ) Notice: Subject to any disclaimer, the term of this patent is extended or adjusted under 35 U.S.C. 154(b) by 819 days.

(21) Appl. No.: 17/044,592

(22) PCT Filed: Apr. 3, 2019

(86) PCT No.: PCT/EP2019/058361
§ 371 (c)(1),
(2) Date: Oct. 1, 2020

(87) PCT Pub. No.: WO2019/193030
PCT Pub. Date: Oct. 10, 2019

(65) Prior Publication Data
US 2021/0024863 A1  Jan. 28, 2021

(30) Foreign Application Priority Data

Apr. 3, 2018 (DE) .................... 10 2018 107 810.2

(51) Int. Cl.
*C12M 1/22* (2006.01)
*B01L 3/00* (2006.01)
(Continued)

(52) U.S. Cl.
CPC ........... *C12M 23/10* (2013.01); *B01L 3/5085* (2013.01); *C12M 23/08* (2013.01); *C12M 23/22* (2013.01);
(Continued)

(58) Field of Classification Search
CPC ...... C12M 23/10; C12M 23/08; C12M 23/22; C12M 41/00; B01L 3/5085;
(Continued)

(56) References Cited

U.S. PATENT DOCUMENTS

| 4,863,759 A | * | 9/1989 | Warde | .................... | H01J 31/065 |
| | | | | | 118/410 |
| 10,088,443 B2 | * | 10/2018 | Schmidt | ............. | G01N 33/5438 |

(Continued)

FOREIGN PATENT DOCUMENTS

| DE | 10048997 A1 | 4/2002 |
| DE | 10217569 A1 | 11/2003 |
| WO | 2013029609 A2 | 3/2013 |

OTHER PUBLICATIONS

International Preliminary Report on Patentability for International Application No. PCT/EP2019/058361 dated Oct. 3, 2020 and Written Opinion of the International Searching Authority dated Jul. 23, 2019.

(Continued)

*Primary Examiner* — Roy M Punnoose
(74) *Attorney, Agent, or Firm* — Heslin Rothenberg Farley & Mesiti P.C.; Nicholas Mesiti

(57) ABSTRACT

A transparent specimen slide on which the range and the magnitude of the near-surface electrostatic forces can be influenced and set during a process of producing the specimen slide. The specimen slide has a surface on the supporting side and a surface facing away from the supporting side and at least three layers: an electrically insulating first layer, (Continued)

a silicon-containing second layer arranged on the first layer, and an electrically insulating third layer arranged on the second layer. An interface is formed between the first and second layers and between the second and third layers with a first surface charge density. The interface between the second and third layers has a second surface charge density. The first and second surface charge densities have the same or different signs.

20 Claims, 12 Drawing Sheets

(51) Int. Cl.
    *C12M 1/24*     (2006.01)
    *C12M 1/00*     (2006.01)
    *C12M 1/34*     (2006.01)
    *G01N 27/22*     (2006.01)

(52) U.S. Cl.
    CPC ............ *C12M 41/00* (2013.01); *G01N 27/226* (2013.01); *B01L 2300/0645* (2013.01); *B01L 2300/0822* (2013.01); *B01L 2300/0829* (2013.01); *B01L 2300/168* (2013.01)

(58) Field of Classification Search
    CPC ..... B01L 2300/0645; B01L 2300/0822; B01L 2300/0829; B01L 2300/168; B01L 2300/0654; B01L 2300/163; B01L 3/508; G01N 27/226; G01N 27/02
    See application file for complete search history.

(56) References Cited

U.S. PATENT DOCUMENTS

| | | |
|---|---|---|
| 2004/0028875 A1 | 2/2004 | Van Rijn et al. |
| 2009/0020428 A1 | 1/2009 | Levitan et al. |
| 2010/0140497 A1 | 6/2010 | Damiano, Jr. et al. |
| 2014/0291143 A1* | 10/2014 | Schmidt ............... G01N 27/327 204/279 |
| 2016/0334962 A1 | 11/2016 | Chen et al. |

OTHER PUBLICATIONS

International Search Report (and English translation) and Written Opinion of the International Searching Authority for International Application No. PCT/EP2019/058361 dated Jul. 23, 2019.

Chiou, P.Y., et al., "Massively parallel manipulation of single cells and microparticles using optical images", Nature, vol. 436, pp. 370-372 (2005).

Schmidt, H., "Designing smart carriers for biosensors, tissue engineering, and directed cell growth by teaming up semiconductor wafers from micro/nano-electronics and polymer supports from biotechnology", Retrieved from the Internet: https://d2cax41o7ahm51.cloudfront.net/cs/speaker-ppts/heidimarie-schmidt-chemnitz-university-of-technology-germany.ppt, Retrieved Jul. 5, 2019, Whole document.

\* cited by examiner

Fig. 7
Bottom Plate for Bottomless Microtiter Plate or Bottomless Microgrid
A (Side View)
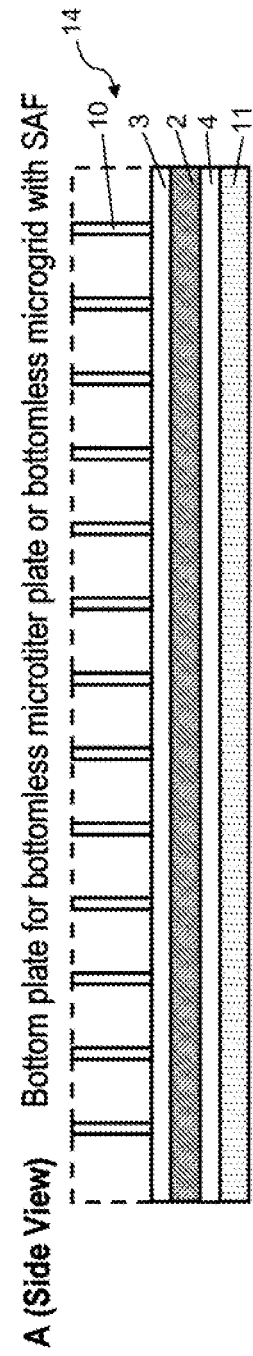
B (Zoom-in Side View)
Individual well of a microtiter plate/microgrid with SAF
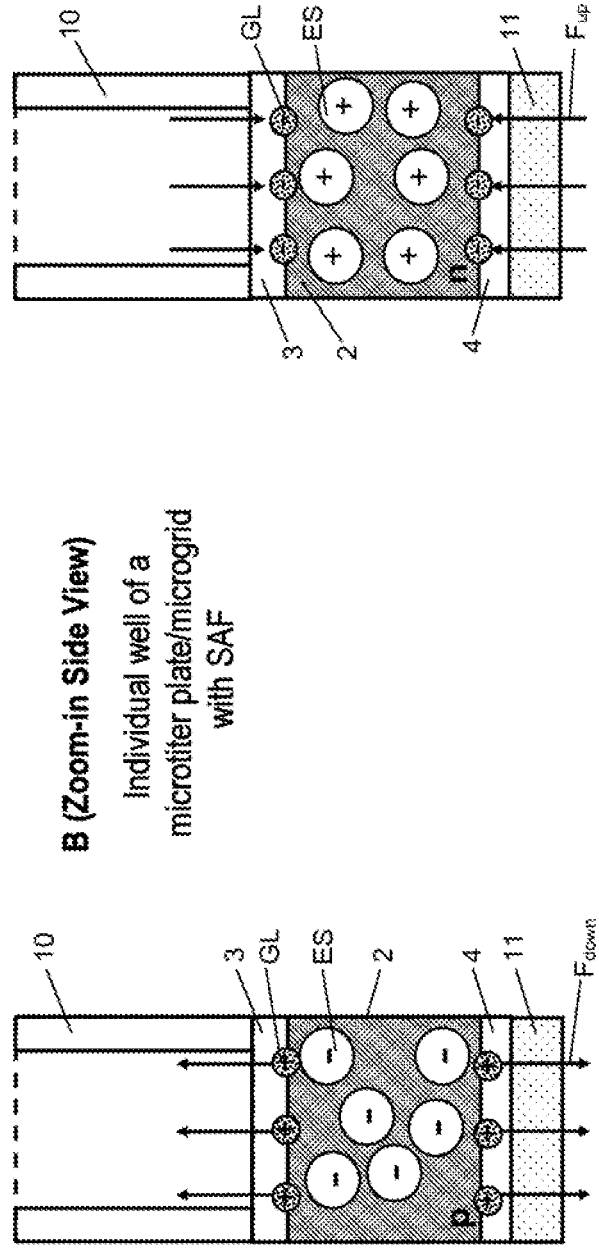

TRANSPARENT SPECIMEN SLIDE

CROSS REFERENCE TO RELATED APPLICATIONS

This application is the National Phase filing under 35 U.S.C. § 371 of International Application No. PCT/EP2019/058361, filed on Apr. 3, 2019, and published on Oct. 10, 2019 as WO 2019/193030 A1, which claims priority to German Application No. 102018107810.2, filed on Apr. 3, 2018. The contents of each of the prior applications are hereby incorporated by reference herein in their entirety.

The invention relates to a transparent object carrier that may be used in biotechnology and in a method for impedance measurement.

BACKGROUND

Carrier materials based on semiconductors, having electrically activated charge patterns, as well as based on ferroelectric or piezoelectric materials, are described in WO 2013/029609 A1. These carrier materials are used for the manipulation, modification and movement of electrically polarizable materials by means of near-surface electrostatic forces. The fundamental common technical feature of the prior art is the use of near-surface electrostatic forces that are induced by the doped semiconductor material or by the piezoelectric or ferroelectric materials. The pattern of the near-surface electrostatic forces is dictated by the pattern of the electrically activated dopant ions in the semiconductor material. In the case of doped semiconductor materials having an optional rear-side electrode, very small voltages are sufficient to vary or minimize the near-surface electrostatic forces. WO 2013/029609 A1 describes that, owing to the optional use of an insulating cover layer on the carrier materials, the near-surface electrostatic forces are not influenced by the electrically polarizable biomaterials, polyelectrolyte materials, atoms, ions and molecules (abbreviated to: epAIM), even if they are present in a liquid medium.

With the carrier material described in WO 2013/029609 A1, the range of the near-surface electrostatic forces above the carrier material cannot, however, be influenced further after the introduction of the electrically active ions. Furthermore, the carrier material is not transparent for light in the visible spectral range, and so observation of the materials adsorbed on the carrier material because of the near-surface electrostatic forces by means of transmission light microscopy is not possible according to the current state of the art. Furthermore, it is disadvantageous that the carrier material is mechanically rigid and not elastically shapeable. Flexible use in biotechnology products is therefore not possible.

The object of the present invention is therefore that of providing an object carrier which does not have the stated disadvantages of the prior art and on which the range and the strength of the near-surface electrostatic forces, which the object carrier has after production, may be variably adjusted and influenced.

SUMMARY OF THE INVENTION

The object is achieved by a transparent object carrier, which comprises a supporting-side surface suitable for supporting a measurement object and a surface facing away from the supporting side, i.e. a rear-side surface, and at least three layers: an electrically insulating first layer, a silicon-containing second layer arranged on the first layer, and an electrically insulating third layer arranged on the second layer, wherein an interface is respectively formed between the first layer and the second layer and between the second layer and the third layer, wherein the interface between the first layer and the second layer has a first surface charge density and the interface between the second layer and the third layer has a second surface charge density, wherein the first and second surface charge densities have the same or different signs and the object carrier has near-surface electrostatic forces on both surface sides, the range and strength of which may be influenced and adjusted during the production process.

A supporting-side surface of the transparent object carrier is intended to mean the surface that is directed toward a measurement object to be studied and, for example, is suitable for being in direct contact with the measurement object, or intended and suitable for supporting a measurement object. Correspondingly, a rear-side surface facing away from the supporting side is intended to mean the surface of the transparent object carrier that does not face toward a measurement object and lies opposite, i.e. on the other side from, the supporting side of the object carrier.

A surface charge density describes the charge distribution in an interface. Depending on whether positive or negative charges are present, positive or negative values are possible for the surface charge densities. If homonymous charges are present for the first and second surface charge densities, the two surface charge densities have the same sign, and if nonhomonymous charges are present for the first and second surface charge densities, the two surface charge densities have different signs. In what follows, the absolute value of the surface charge density is referred to as the strength of the surface charge density.

The object carrier according to the invention is transparent and may optionally be configured to be flexibly deformable. For example, the object carrier may be configured to be transparent in such a way that it has a transmittance of more than 5% in the spectral range having wavelengths of more than 200 nm, with a transmittance of more than 10% in the spectral range having wavelengths of more than 350 nm, and with a transmittance of more than 15% in the spectral range having wavelengths of more than 400 nm. A glass sheet may, for example, be the electrically insulating third layer or be used below the electrically insulating third layer.

Because of the transparency, with this object carrier electrically polarizable materials may be observed by means of transmission light microscopy. The transparency is achieved by using the at least three thin layers, namely the electrically insulating first layer, the silicon-containing second layer and the electrically insulating third layer. In the context of this invention, a thin layer is intended to mean a layer thickness of less than 1 μm.

According to the laws of optics in solids, the probability of the absorption of light per unit length in an absorbing homogeneous semiconductor for low energies is the same at every penetration depth. An exponential law then applies, the Beer-Lambert law, which states that the original light intensity I0 after passing through the layer thickness d has the remaining light intensity I(d):

$$I(d)/I0 = e^{-(\mu d)},$$

where μ is the absorption coefficient and depends on the properties of the absorbing material. The inverse of the absorption coefficient is the penetration depth.

According to the laws of defects in solids, the range of the near-surface electrostatic forces above a semiconductor material is at most as great as the extent dDL of the near-surface space charge zone in the semiconductor. Here, for the case in which the space charge zone at the interface between the first and second layers does not overlap with the space charge zone at the interface between the second and third layers, the range of the electrostatic forces on the supporting-side surface of the object carrier may be equated with the extent $dDL,top$ of the space charge zone at the interface between the second and third layers, and the range of the electrostatic forces on the rear-side surface, facing away, of the object carrier may be equated with the extent $dDL,bottom$ of the space charge zone at the interface between the first and second layers.

In summary, the strength of the near-surface electrostatic forces depends substantially on the one hand on the distance of the interfaces between the first and second layers and between the second and third layers from one another, and on the other hand on the surface charge densities at the respective interface as well as on the doping of the silicon-containing material from which the silicon-containing second layer is formed. In this case, a silicon-containing layer is intended to mean a layer that contains a proportion of at least 1 at.v% (atomic percent) silicon.

In advantageous configurations of the object carrier according to the invention, the strength of the first surface charge density is greater than the strength of the second surface charge density, or the strength of the first surface charge density is less than the strength of the second surface charge density, or the strength of the first surface charge density and the strength of the second surface charge density are equal. The strength and range of the near-surface electrostatic forces on the supporting-side surface of the transparent object carrier and on the rear-side surface of the object carrier may therefore be adjusted.

The silicon-containing layer represents a source of near-surface electrostatic forces, locally adjustable during the production process, by which electrically polarizable materials can be adsorbed and/or desorbed. The direction and strength of the near-surface electrostatic forces on the surface of the transparent object carrier are adjusted by the selection of the species (electrons or holes) and/or concentration of the majority charge carriers in the locally doped silicon-containing layer.

The surface charge density between the electrically insulating first layer and the silicon-containing second layer containing the dopant ions of various species, for example phosphorus or boron, as well as the surface charge density between the electrically insulating third layer and the silicon-containing second layer containing the dopant ions, induce the near-surface electrostatic forces both on the supporting-side surface of the object carrier and on the rear-side surface, facing away from the supporting side, of the transparent object carrier according to the invention with a different range. The thicknesses $dISO,top$ and $dISO,bottom$ of the electrically insulating first and third layers likewise determine the strength of the near-surface electrostatic forces. Typically, the strength, direction and range of the electric field depends on the pattern of the interfacial states and may be modified during the production of the transparent object carrier. The range of the electrostatic forces, according to the equating with the extent $dDL,bottom$ of the space charge zone at the interface between the first and second layers on the rear-side surface and with the extent $dDL,top$ of the space charge zone at the interface between the second and third layers on the supporting-side surface of the object carrier, is between 1 nm and 2000 nm, and according to the equating with the extent of the space charge zone is at most equal to the thickness of the object carrier.

That is to say, the range of the near-surface electrostatic forces is adjusted by modifying the surface charge densities in at least one of the two interfaces, either between the rear-side electrically insulating first layer and the silicon-containing second layer, or between the supporting-side electrically insulating third layer and the silicon-containing second layer.

In general, a thin layer or a plurality of thin layers of various materials may be deposited by means of suitable production methods on a transparent substrate or on a carrier. In this case, it is possible to use production methods such as, for example, physical vapor deposition (PVD), physical cathode sputtering and chemical vapor deposition (CVD), these methods being usable in many different versions, for example as pulsed laser deposition (PLD), sputtering, electron beam evaporation, molecular beam epitaxy, plasma-enhanced chemical vapor deposition (PECVD), and other methods. Either a substrate may be used as a carrier during the production of the transparent object carrier, which is subsequently removed, or it may remain on the transparent object carrier for stabilization on the rear-side surface, facing away from the supporting side, of the object carrier. Then, however, the substrate should likewise be transparent.

In general, an electrically insulating thin layer may be deposited on a transparent substrate. In general, a semiconductor layer of varying thickness may be deposited on an electrically insulating thin layer, in which case a charge pattern may be introduced into the semiconductor layer during the layer deposition and/or after the layer deposition by means of ion implantation. Two interfaces having so-called space charge zones are formed in the thin semiconductor layer. According to the invention, on the one hand a space charge zone facing away from the supporting-side surface of the object carrier, and on the other hand a space charge zone facing toward the supporting-side surface, are respectively formed at the interface between the electrically insulating first layer and the silicon-containing second layer and between the electrically insulating third layer and the silicon-containing second layer, the space charge zones respectively having a thickness of from 1 nm to 2000 nm, preferably from 10 nm to 500 nm.

In a further configuration of the transparent object carrier according to the invention, the near-surface electrostatic forces on the supporting-side surface and the near-surface electrostatic forces on the rear-side surface of the object carrier point in the same direction, the range of the near-surface electrostatic forces being adjusted by the ratio of a total thickness of the silicon-containing second layer to the sum of the extent of the space charge zone at the interface between the rear-side electrically insulating first layer and the silicon-containing second layer and the extent of the space charge zone at the interface between the electrically insulating third layer, facing toward the supporting side, and the silicon-containing second layer, such that the range of the near-surface electrostatic forces on the supporting-side surface and on the rear-side surface of the object carrier is comparatively as great as the extent of the sum of the two space charge zones. This has the particular advantage that, in contrast to the prior art, the near-surface electrostatic forces may be enhanced, or varied, by means of two interfaces and surface charge densities. Previously, only non-transparent silicon-containing carriers have been used, and although it has been possible for the near-surface electrostatic forces being formed to be formed on both sides of the silicon-containing layer, they could not be superposed on the supporting-side surface and on the rear-side surface of the object carrier since the total thickness of the object carrier has been greater than the sum of the two space charge zones and has prevented this.

The thickness of the silicon-containing second layer of the object carrier according to the invention is at most 5 µm and, for this thickness of the silicon-containing second layer, has a transmittance of more than 80% in the IR spectral range. The thickness of the object carrier is embodied in such a way that it is transparent with a transmittance of almost 100% in the near infrared. Preferably, the thickness of the object carrier is less than 1 mm, preferably less than 100 µm and particularly preferably less than 10 µm. If the thickness of the object carrier is less than 10 µm, the transmittance is more than 5% in the spectral range having wavelengths of more than 200 nm, more than 10% in the spectral range having wavelengths of more than 350 nm, and more than 15% in the spectral range having wavelengths of more than 400 nm. Optionally, the object carrier is configured to be flexibly deformable. The glass sheet may, for example, be the electrically insulating first layer or it may be used below the electrically insulating first layer.

The thickness of the silicon-containing layer also has an influence on the interaction of the near-surface electrostatic forces, which result from the interfaces and the associated surface charge densities, on the two sides of the object carrier. In this case, it should be noted that if the thickness of the silicon-containing layer is greater than the extent of the two space charge zones, which are formed at the respective interfaces of the first and second layers and of the second and third layers, only the space charge zone facing toward the supporting-side surface of the object carrier and the surface charge density facing toward the supporting-side surface of the object carrier influence the near-surface electrostatic forces. If the thickness of the silicon-containing second layer is equal to or less than the extent of the two space charge zones, both the space charge zone facing toward the supporting-side surface of the object carrier and the rear-side space charge zone facing away from the supporting-side surface, and the respective surface charge densities, influence the near-surface electrostatic forces on the supporting-side surface of the transparent object carrier. This has the advantage that the range of the near-surface electrostatic forces may be increased further.

In general, a semiconductor layer on a transparent substrate may be thermally treated by means of pulsed laser radiation and/or by means of flash lamp annealing both before the introduction of the charge pattern and after the introduction of the charge pattern, in such a way that the crystalline structure of the semiconductor layer with or without a charge pattern is modified such that the thin semiconductor layer is electrically activated. The activation of the electrically active dopant ions in the semiconductor layer is typically carried out only once after the layer deposition. On the other hand, the density of the interfacial states, i.e. the surface charge densities, depends highly sensitively on the treatment of the object carrier at the position of the interface between the thin silicon-containing second layer and the rear-side electrically insulating first layer and at the position of the interface between the thin silicon-containing second layer and the supporting-side electrically insulating third layer. The surface charge densities advantageously lie in the range of from 1012 to 1020 e/cm$^2$.

In one preferred configuration of the transparent object carrier according to the invention, an electrically conductive layer, in particular an electrode, is formed on the supporting-side surface and/or on the rear-side surface of the transparent object carrier. In the context of this invention, an electrically conductive layer is intended to mean a surface or surfaces used for contacting the object carrier for its use in biotechnology.

In a further particularly preferred configuration, the electrically conductive layer is configured to be transparent in sections or fully, the electrically conductive layer, i.e. in particular the configuration as an electrode, being configured for shielding of the near-surface electrostatic forces and/or for contacting. By the configuration or structuring of the electrically conductive layer, the object carrier may be configured and adapted for its field of use.

In general, an electrically conductive thin layer may be deposited on an electrically insulating thin layer. By means of lithography methods, for example electron beam lithography and/or photolithography, electrically conductive thin layers may be structured.

In one preferred configuration of the transparent object carrier according to the invention, the interface between the first layer and the second layer and/or between the second layer and the third layer respectively has an interfacial state pattern that is formed by a spatially/locally varying surface charge density in the respective interface. The surface charge density, the density or magnitude of which may vary in the interface, is also referred to as a charge pattern.

The active defects introduced into the interface or generated therein form the charge pattern, i.e. different densities of interfacial charges form a pattern in the transparent object carrier according to the invention. The pattern of the surface charge densities may be formed or modified in at least one of the two interfaces during the production of the silicon-containing second layer. The interfacial states and the ionized dopant ions in the space charge zone of the silicon-containing second layer generate the electrostatic forces that act. These forces are shielded from the environment at the position of the electrically conductive layers. That is to say, the regions, transparent at least in sections, of the applied electrically conductive layer on the one hand act as shielding of the electrostatic forces, and on the other hand they are used as electrically conductive contacts.

The transparent object carrier according to the invention may therefore in one configuration be used to measure an electrical-capacitive impedance. Modeling of the electrical-capacitive impedance provides information about the influence of the adhesion of material in the region of the contacts on the modeled contact resistance Rs. The electrical impedance may be measured in situ, for example in an incubator, and used for nondestructive observation, for example of the adhesion of biological materials in the region of the contacts on the supporting-side surface of the transparent object carrier.

In order to illuminate an object that has been adsorbed by the electrostatic forces, an optical microscope may be arranged on the rear side, i.e. on the rear-side surface, facing away from the supporting-side surface, of the object carrier in order to observe the object. The light used for the illumination may be polarized. The optical microscope, for example a polarization microscope, may use and detect polarized light for the illumination of the object. The optical microscope, for example a laser scanning microscope, may use and detect laser light for the illumination of the object. The resolution limit of optical microscopes, i.e. the distance d that two points must have between them in order that they can still be perceived as separate points, is $d=\lambda/\text{NAObjective}$. Here, $\lambda$ is the wavelength of the light used for the illumination and NAObjective is the numerical aperture of the objective of the microscope used. The resolution limit of optical microscopes, for example of immersion microscopes, is increased by introducing a liquid between the object and the objective of the microscope.

In a further configuration of the transparent object carrier according to the invention, the transparent object carrier comprises at least two sections, which differently influence a polarization of radiation striking the object carrier. This is advantageous because the resolving power in microscopy may thereby be improved.

It is particularly advantageous for the transparent object carrier according to the invention to be configured as a bottom plate of a microtiter plate or as a bottom plate of a microgrid, or as a Petri dish or as a microscope slide. The precise dimensions (length×width×height) of the microtiter plates may, for example according to the ANSI standard, be 127.76 mm×85.48 mm×14.35 mm. Instead of a bottomless microtiter plate, a microgrid may also be used, for example a 10×20 microgrid with an edge length of 100-200 μm. Petri dishes are flat, round, transparent dishes with a covering lid. Petri dishes are produced in various sizes from laboratory glass and plastic. Commonly used outer diameters are 50 and 92 to 93 mm (=90 mm inner diameter) with a height of 15 mm. In the simplest case, the transparent object carrier forms a microscope slide, which is used in microscopy.

It is likewise particularly advantageous for the transparent object carrier according to the invention to be flexibly configured and to be configured for the cladding of cell culture flasks. Cell culture flasks are widespread in biotechnology.

The invention will be explained in more detail below with the aid of exemplary embodiments.

BRIEF DESCRIPTION OF THE DRAWING FIGURES

In the drawings:

FIG. 7 shows the use of the transparent object carrier according to the invention as a bottom plate for a bottomless microtiter plate or a bottomless microgrid;

Figure 1:
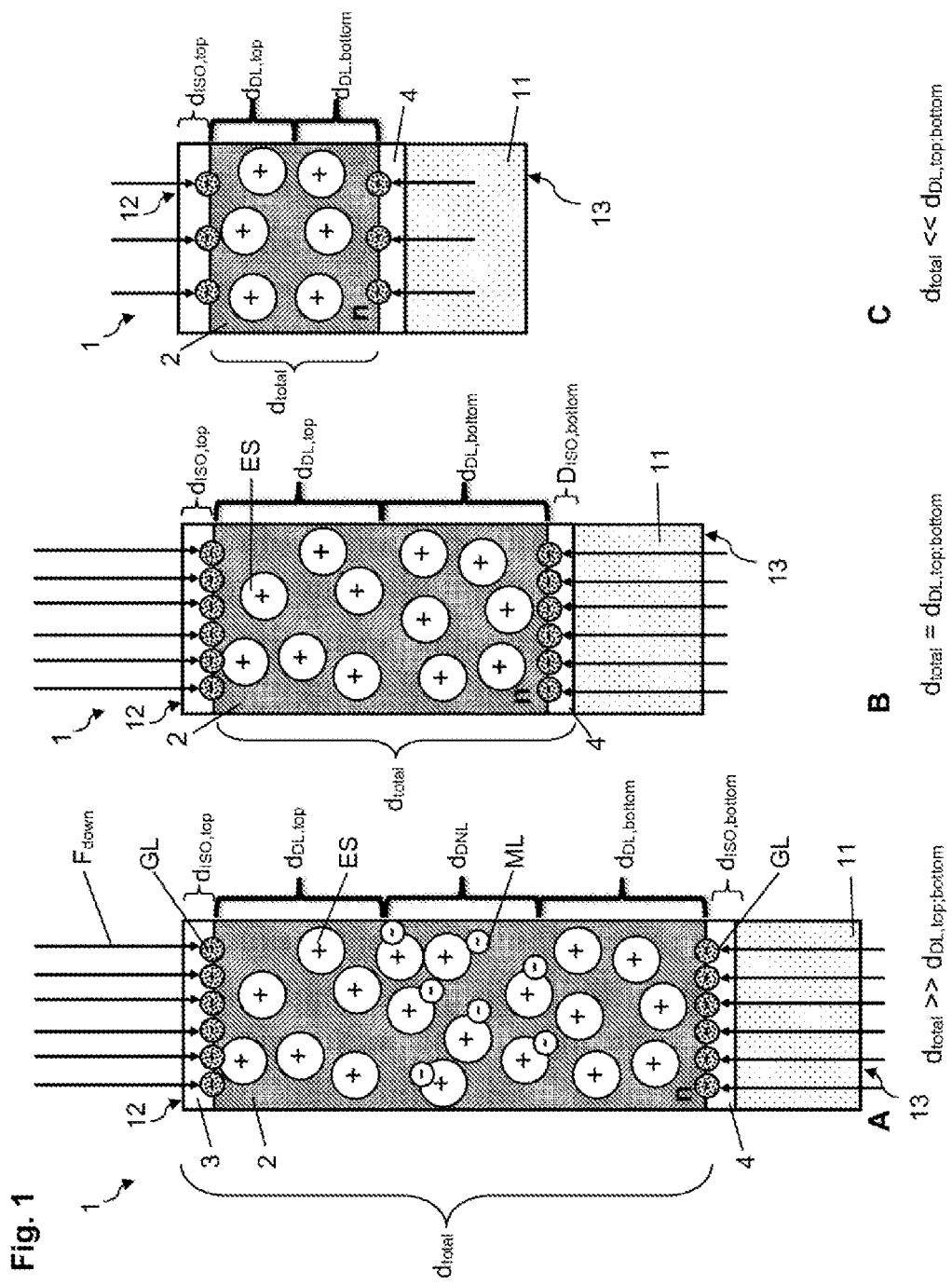
FIG. 1 shows a transparent object carrier having a charge pattern in the n-Si semiconductor and various thicknesses of the Si semiconductor layer.
Figure 3:
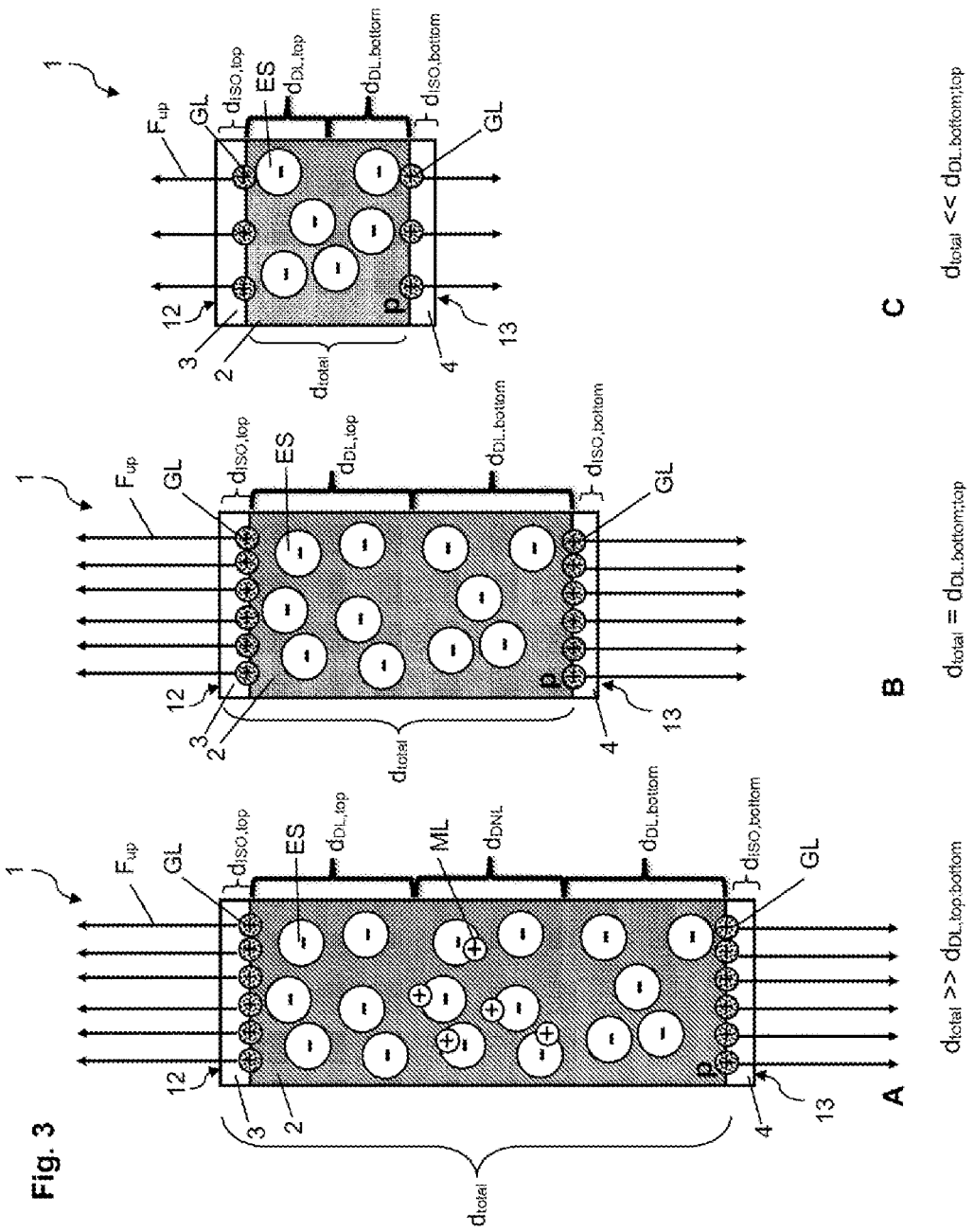
FIG. 3 shows a transparent object carrier having a charge pattern in the p-Si semiconductor and various thicknesses of the Si semiconductor layer.

FIG. 1 shows the transparent object carrier 1 according to the invention with a charge pattern in the n-Si semiconductor and various thicknesses of the silicon-containing layer 2. In FIG. 1A, the thickness dtotal of the silicon-containing second layer 2 is substantially greater than the space charge zones dDL,top and dDL,bottom formed, taken together, while in FIG. 1B the thickness of the silicon-containing second layer 2 is equal to the thickness of the two space charge zones, and in FIG. 1C the thickness dtotal is substantially less than the thickness of the two space charge zones. FIG. 3 shows the same situation for a p-Si semiconductor as the silicon-containing second layer 2. The range of the electrostatic forces may be adjusted by the ratio of a total thickness of the silicon-containing second layer 2 and a thickness of the respective space charge zone between the rear-side dDL,bottom and/or supporting side dDL,top electrically insulating first layer 4 and third layer 3, respectively, and the silicon-containing second layer 2. The thickness of the silicon-containing second layer 2, which is about 1 μm when it is intended to be transparent for radiation in the visible to infrared wavelength range, may be greater than the extent of the two space charge zones dDL,top and dDL,bottom. In this case, only the respective space charge zone and the surface charge density influence the near-surface electrostatic forces of the respective surface of the object carrier 1. The thickness of the silicon-containing second layer 2 may also be equal to or less than the extent of the two space charge zones dDL,top and dDL,bottom. In these cases, both the supporting-side space charge zone dDL,top and the rear-side space charge zone dDL,bottom, as well as the supporting-side and rear-side surface charge densities influence the near-surface electrostatic forces on the supporting-side surface 12 of the object carrier 1. This has the crucial advantage that the range of the near-surface electrostatic forces may be increased further.

The transparent object carrier 1 may optionally be applied on a flexible or rigid, transparent or opaque substrate 11, shown by way of example in FIG. 1. The substrate 11 therefore represents a carrier for the transparent object carrier 1. This is also possible for the exemplary embodiments in the subsequent figures, the substrate 11 sometimes having been omitted for reasons of clarity.

Figure 2:
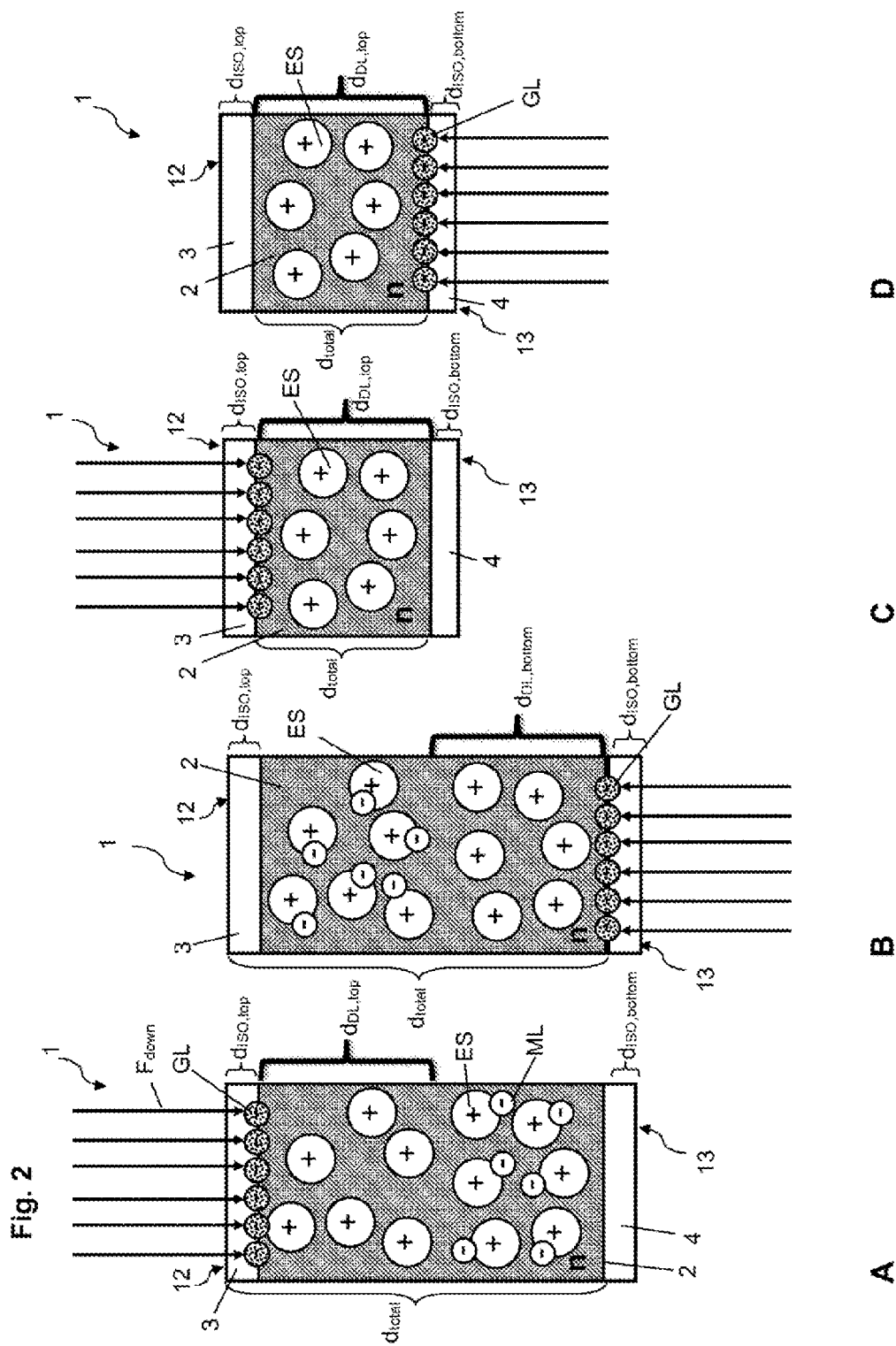
FIG. 2 shows a transparent object carrier having a charge pattern in the n-Si semiconductor and modification of the surface charge densities.
Figure 4:
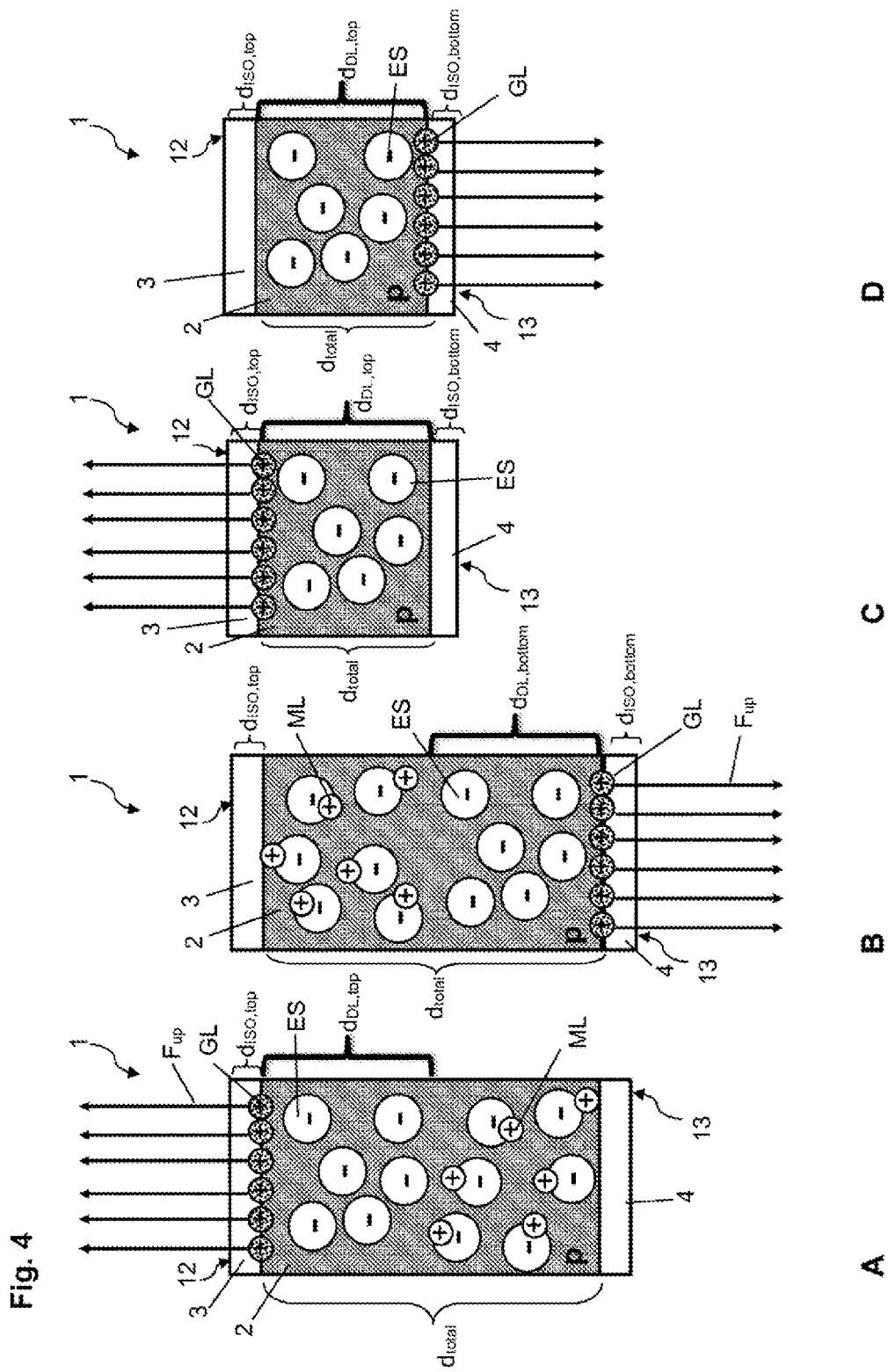
FIG. 4 shows a transparent object carrier having a charge pattern in the p-semiconductor and modification of the surface charge densities.

FIG. 2 shows the transparent object carrier 1 according to the invention with a charge pattern in the n-Si semiconductor, with a modification of the interfacial state densities, or surface charge densities. The greater the state densities are at the interface between the electrically insulating first layer 4 and the silicon-containing second layer 2, or between the electrically insulating third layer 3 and the silicon-containing second layer 2, the greater are the near-surface electrostatic forces that are formed. In the case of an n-Si semiconductor, the forces act attractively, and in the case of a p-Si semiconductor, they act repulsively (force arrow direction). FIG. 4 shows the situation for a p-semiconductor.

Figure 5:
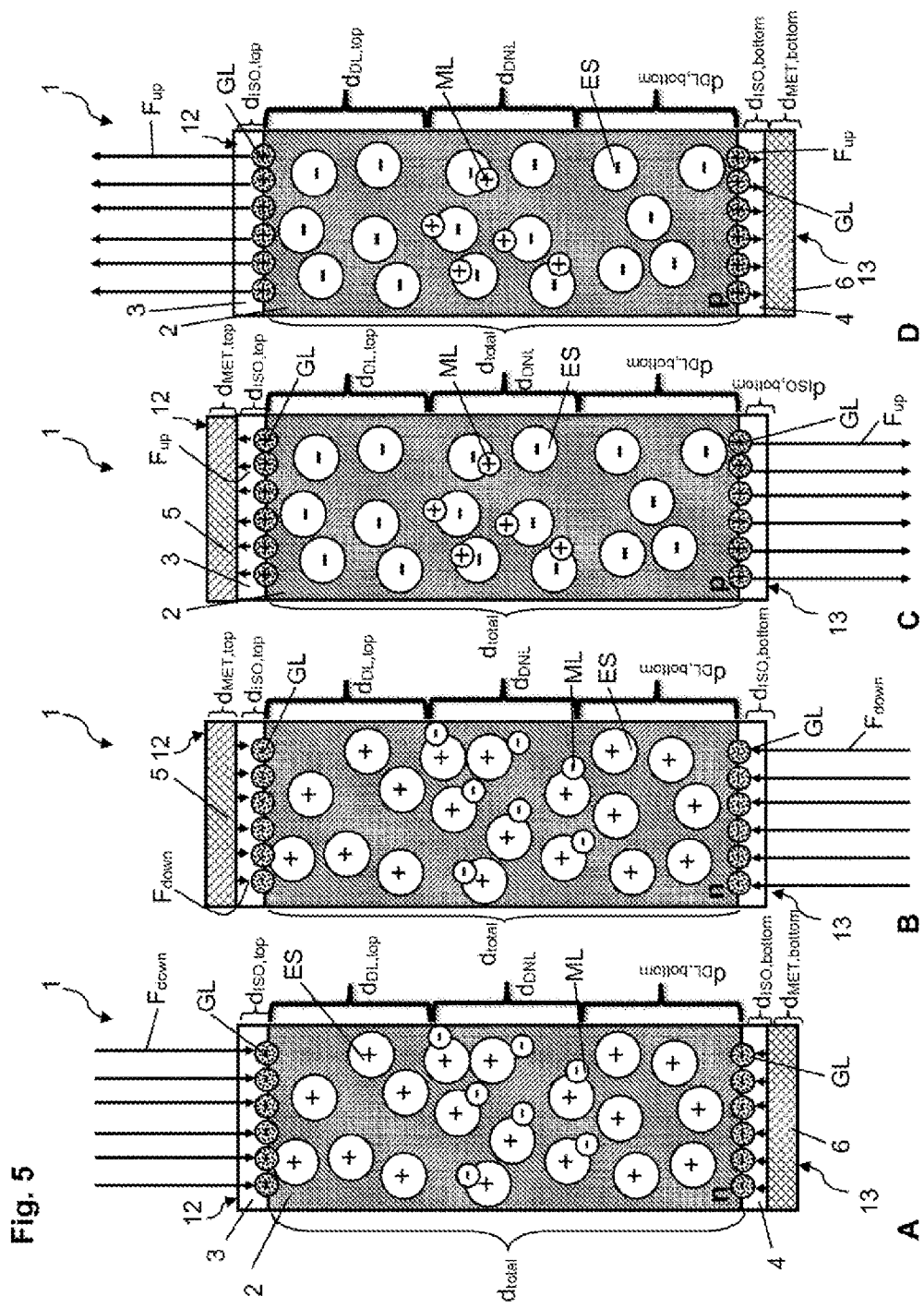
FIG. 5 shows a transparent object carrier having electrically conductive layers and a charge pattern in the n- and p-Si semiconductors.

FIG. 5 shows the transparent object carrier 1 with electrically conductive layers and a charge pattern in the n- and p-Si semiconductors. The electrostatic forces are shielded by the conductive layer 5, 6.

Figure 6:
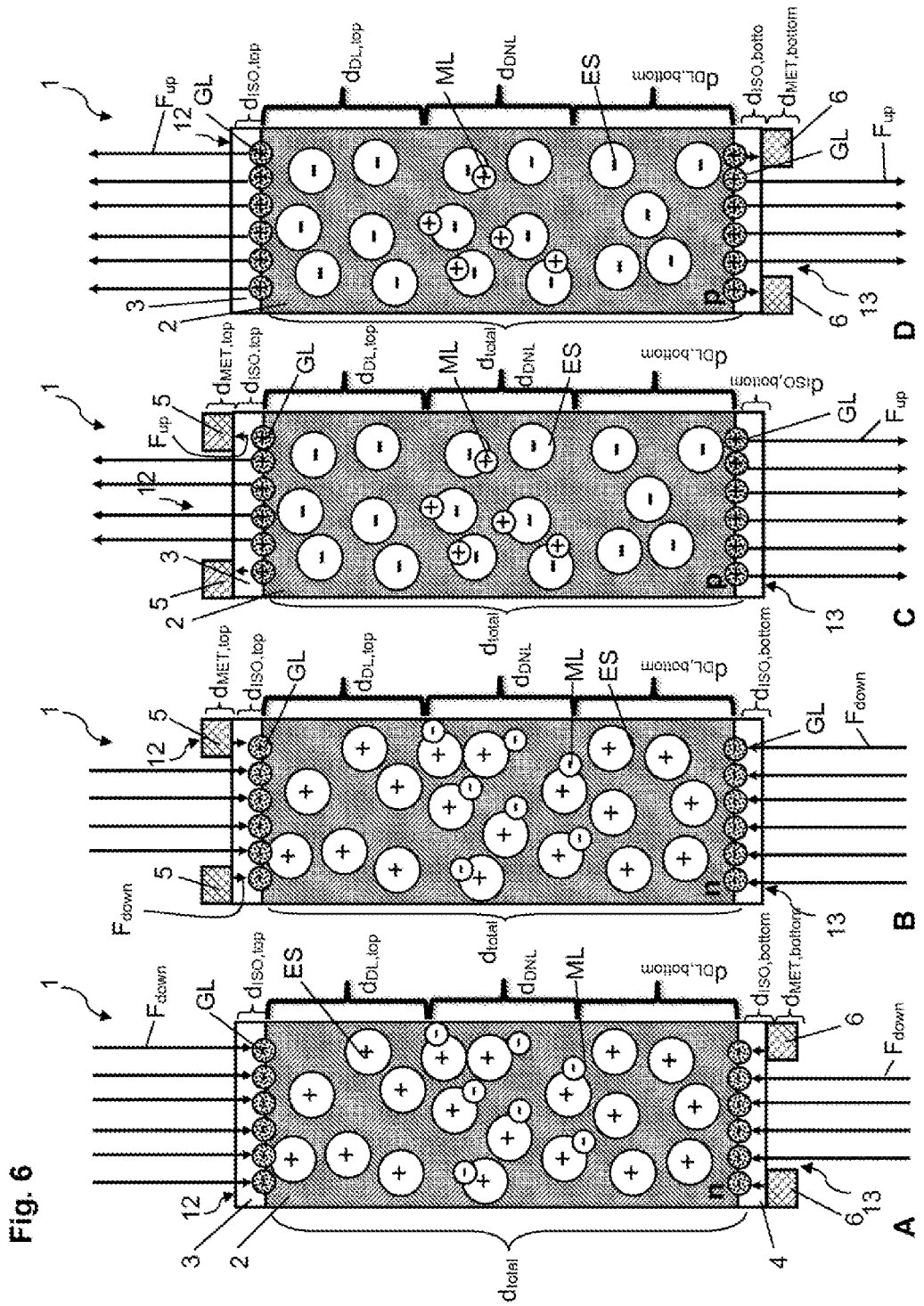
FIG. 6 shows a transparent object carrier having electrically conductive layers configured as electrodes and a charge pattern in the n- and p-Si semiconductors.
Figure 11:
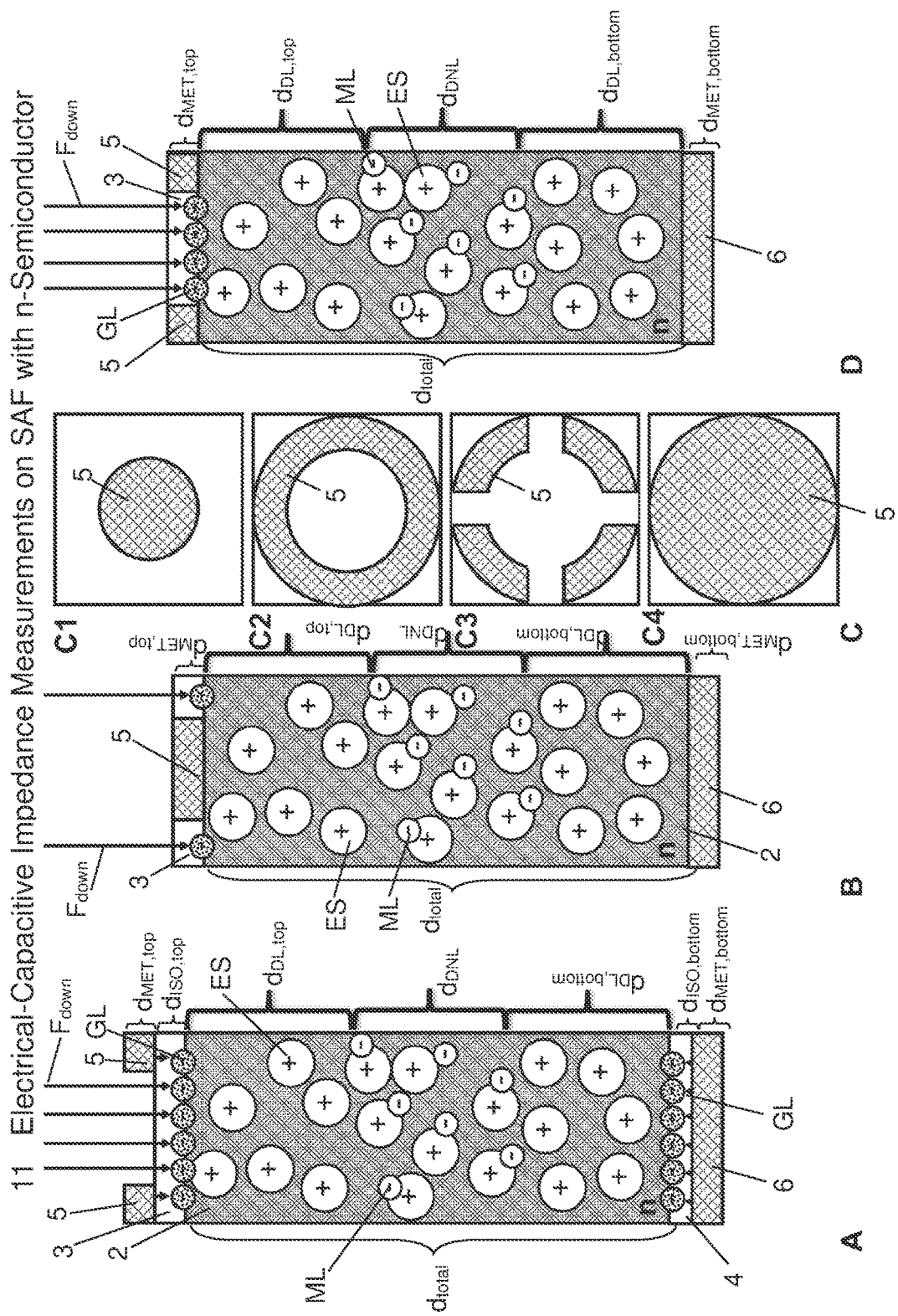
FIG. 11 shows an electrical-capacitive impedance measurement in an n-Si semiconductor.
Figure 12:
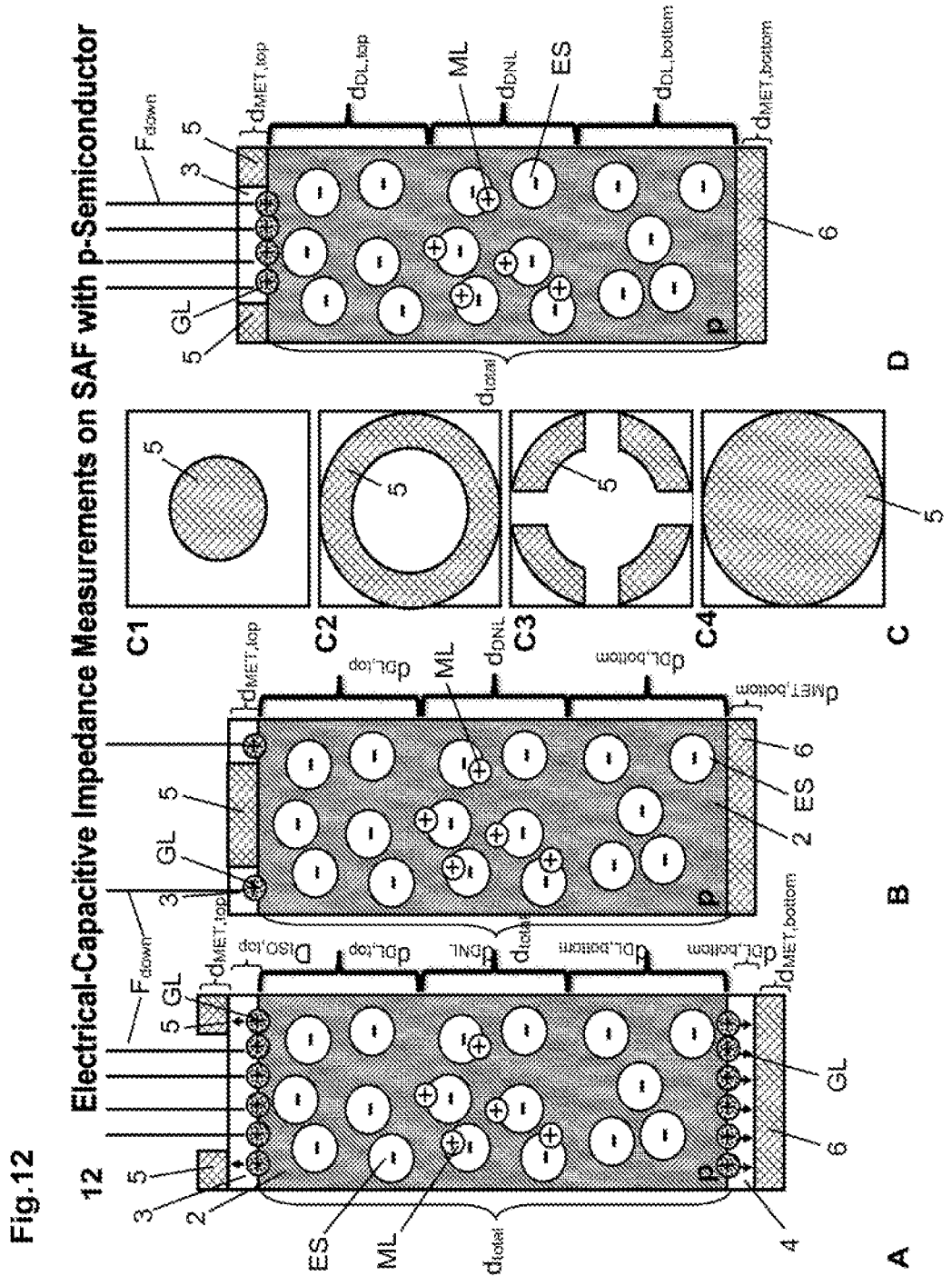
FIG. 12 shows an electrical-capacitive impedance measurement in a p-Si semiconductor.

By structuring of these electrically conductive layers 5, 6, for example by means of lithography methods, for example electron beam lithography and/or photolithography, the electrically conductive layers 5, 6 may also be used as contacts, as is shown in FIG. 6. In one configuration, therefore, the transparent object carrier 1 according to the invention may be used to measure an electrical-capacitive impedance. Modeling of the electrical-capacitive impedance provides information about the influence of the adhesion of material in the region of structured contacts on the modeled contact resistance Rs. In contrast to light microscopes, which do represent a standard method for the studying of biological materials, the electrical-capacitive impedance measurement with the object carrier according to the invention and the integrated structured electrodes offers the advantage that this structure is particularly suitable for long-term studies, there are no restrictions in respect of sterilization, incubation and freezing, and the biological material does not need to be illuminated. The electrical impedance may be measured in situ, for example in an incubator, and used for nondestructive observation, for example of the adhesion of biological materials in the region of structured contacts on the supporting-side surface of the transparent object carrier. FIGS. 11 and 12 show use in an electrical-capacitive impedance measurement with differently structured electrically conductive layers 5, 6, which are configured as contact surfaces. The contact surfaces may for example be circular, annular or configured as divided ring electrodes. This has the advantage that the sensitivity of the total impedance as a function of the occupancy of the electrodes with material may therefore be adjusted.

FIG. 7 shows a particular exemplary embodiment, in which the object carrier 1 according to the invention is used as a bottom plate for a bottomless microtiter plate 14 or for a bottomless microgrid. This is particularly advantageous because the materials to be studied can adhere on the transparent object carrier 1 and, because of the transparency provided, studied for example by means of a transmission light microscope. When the transparent object carrier 1 is used in a microgrid, the regions on which the materials to be studied adhere may be separated from one another by means of freely selectable walls, which form the so-called microgrid (which consists of individual so-called wells 10). These walls 10 may, for example, be made from silicone.

Figure 8:
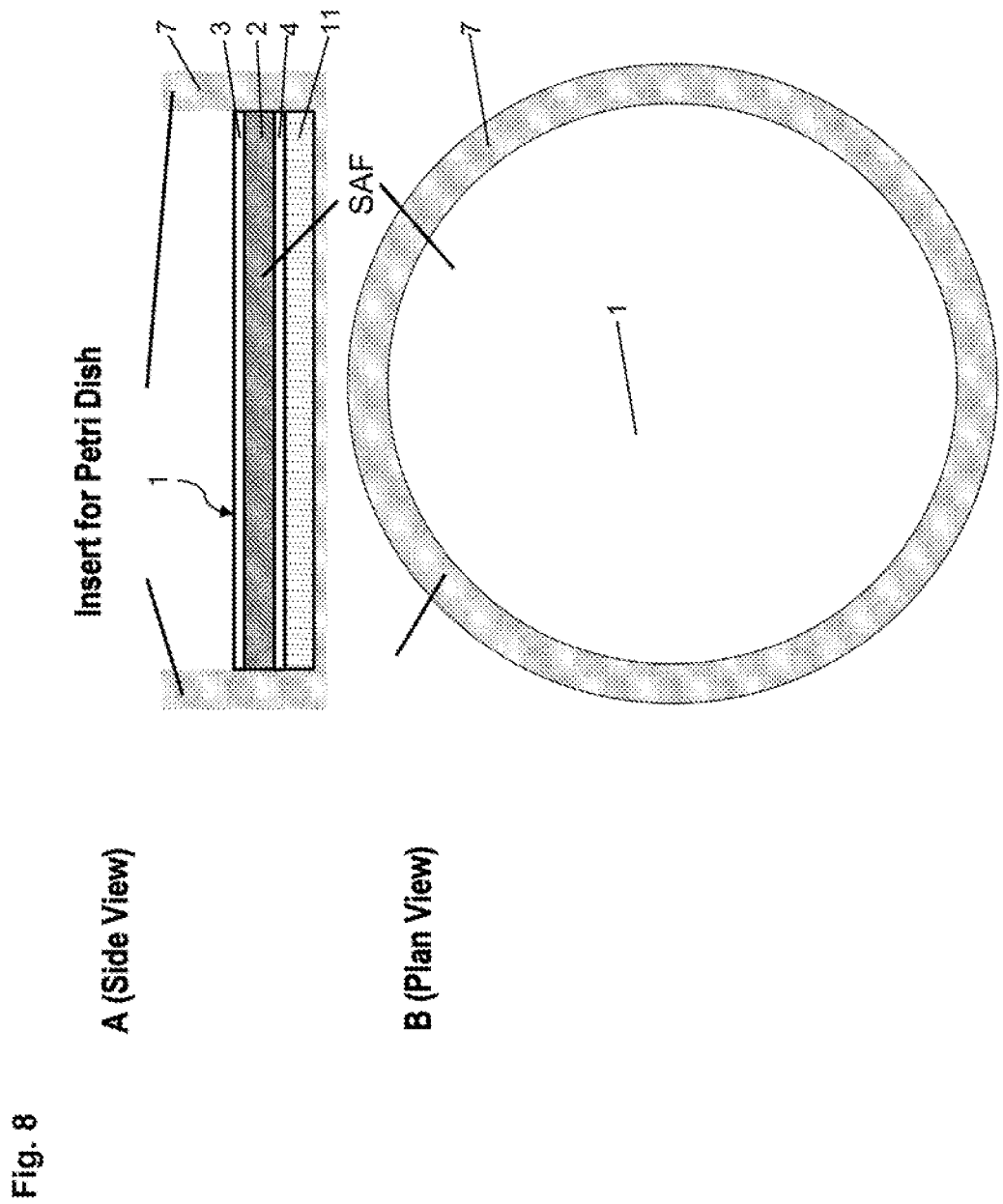
FIG. 8 shows the use of the transparent object carrier according to the invention in a Petri dish.
Figure 9:
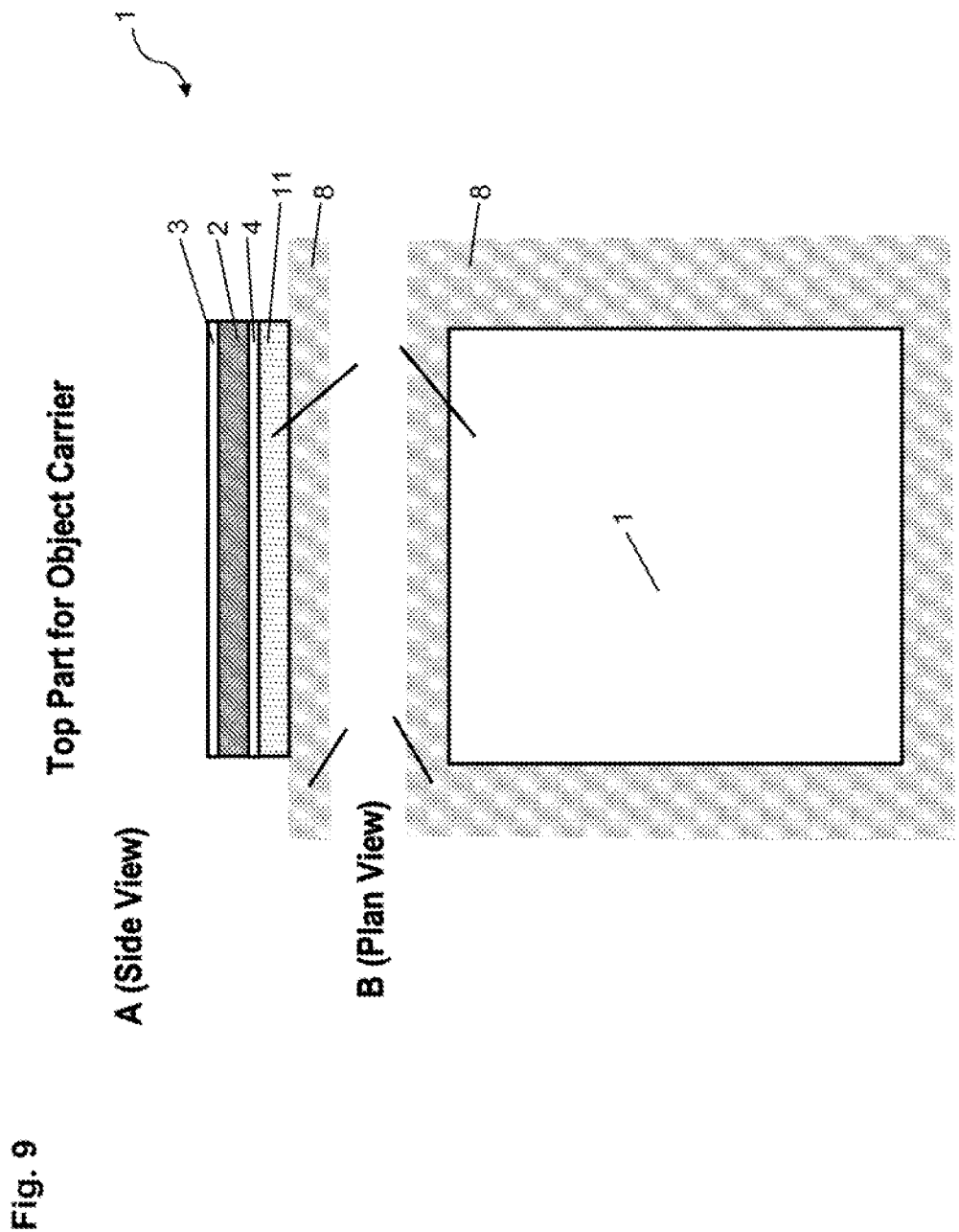
FIG. 9 shows the use of the transparent object carrier according to the invention as a microscope slide.

FIGS. 8 and 9 likewise show particular application examples, in which the object carrier 1 according to the invention is used in or configured as a Petri dish 7 or as a top part for an object carrier.

Figure 10:
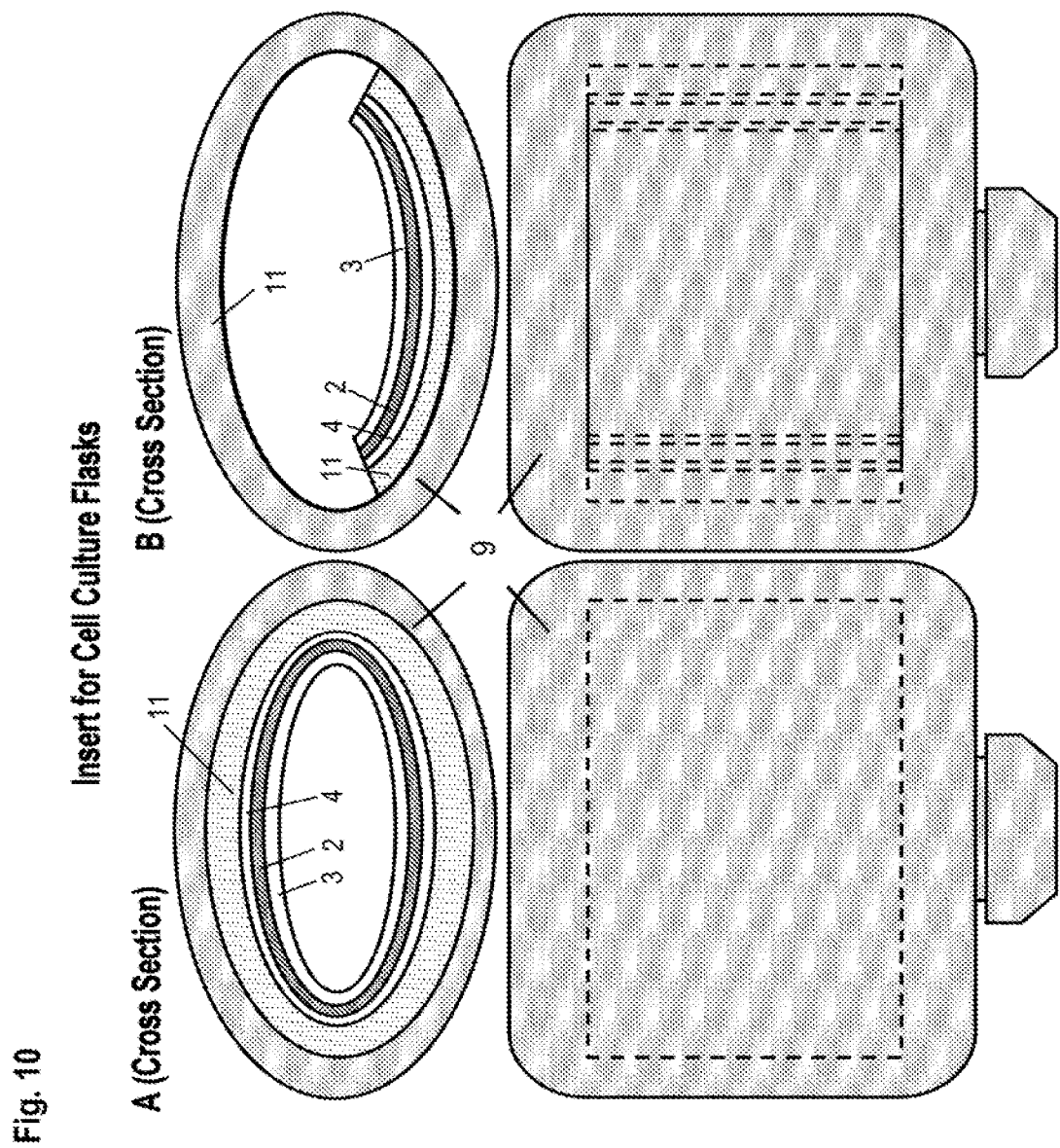
FIG. 10 shows the use of the transparent object carrier according to the invention in a cell culture flask.

Owing to the flexibility of the transparent object carrier 1 according to the invention, it may also be used in a cell culture flask 9. This is schematically represented in FIG. 10.

TRANSPARENT SPECIMEN SLIDE

List of References 1 transparent object carrier
2 silicon-containing second layer of thickness $d_{total}$
3 electrically insulating third layer of thickness $d_{ISO,top}$
4 electrically insulating first layer of thickness $d_{ISO,bottom}$
5 electrically conductive layer of thickness $d_{MET,top}$ adjacent to the third layer
6 electrically conductive layer of thickness $d_{MET,bottom}$ adjacent to the first layer
7 Petri dish
8 object carrier
9 cell culture flask
10 wall of a study region, a so-called well
11 transparent substrate
12 supporting-side surface of the object carrier
13 rear-side surface of the object carrier
14 bottom plate of a microtiter plate
ES electrically active defect, dopant in the semiconductor
ML majority charge which shields an electrically active defect
GL majority charge which occupies an interfacial state
DLtop space charge zone at the interface between the electrically insulating first layer and the silicon-containing second layer, of thickness $d_{DL,top}$
DLbottom space charge zone at the interface between the electrically insulating third layer and the silicon-containing second layer, of thickness $d_{DL,bottom}$
DNL region in the silicon-containing layer in which no space charge zone is formed, of thickness $d_{DNL}$

The invention claimed is:

1. A transparent object carrier for transferring light, comprising:
    a supporting-side surface for supporting a measurement object, and a rear-side surface, facing away from the supporting side, and at least three layers comprising:
    an electrically insulating first layer,
    a silicon-containing second layer, which contains at least 1 atomic percent silicon, arranged on the first layer, and
    an electrically insulating third layer arranged on the second layer,
    wherein an interface is respectively formed between the first layer and the second layer and between the second layer and the third layer,
    wherein the interface between the first layer and the second layer has a first surface charge density and the interface between the second layer and the third layer has a second surface charge density,
    wherein the first and second surface charge densities have the same or different signs and near-surface electrostatic forces, the range and strength of which are adjusted during the production process, to form on surface sides of the object carrier, such that the electrostatic forces are embodied on both sides or on one side,
    wherein the at least three layers each have a layer thickness of less than 1 µm.

2. The transparent object carrier as claimed in claim 1, wherein the strength of the first surface charge density is greater than the strength of the second surface charge density, or the strength of the first surface charge density is less than the strength of the second surface charge density, or the strength of the first surface charge density and the strength of the second surface charge density are equal.

3. The transparent object carrier as claimed in claims 1, wherein a surface charge density is from $10^{12}$ to $10^{20}$ e/cm$^2$.

4. The transparent object carrier as claimed in claim 1, wherein an electrically conductive layer, in particular an electrode, is formed on the supporting-side surface and/or on the rear-side surface of the transparent object carrier.

5. The transparent object carrier as claimed in claim 4, wherein the electrically conductive layer is configured to be transparent at least in sections, the electrically conductive layer being configured as shielding of the near-surface electrostatic forces and/or for contacting.

6. The transparent object carrier as claimed in claim 1, wherein the interface between the first layer and the second layer and/or between the second layer and the third layer respectively has an interfacial state pattern that is formed by a spatial and locally varying surface charge density in the respective interface.

7. The transparent object carrier as claimed in claim 1, wherein the transparent object carrier comprises at least two sections, which differently influence a polarization of radiation striking the object carrier.

8. The transparent object carrier as claimed in claim 1, wherein the layer system is used to measure an electrical-capacitive impedance.

9. The transparent object carrier as claimed in claim 1, wherein the object carrier is configured as a bottom plate of a microtiter plate or of a microgrid, or is configured as a Petri dish or is configured as a microscope slide.

10. The transparent object carrier as claimed in claim 1, wherein the object carrier is flexibly configured and is configured for the cladding of cell culture flasks.

11. The transparent object carrier as claimed in claim 10, wherein the interface between the first layer and the second layer and/or between the second layer and the third layer respectively has an interfacial state pattern that is formed by a spatial and locally varying surface charge density in the respective interface.

12. The transparent object carrier as claimed in claim 11, wherein the transparent object carrier comprises at least two sections, which differently influence a polarization of radiation striking the object carrier.

13. The transparent object carrier as claimed in claim 12, wherein the layer system is used to measure an electrical-capacitive impedance.

14. The transparent object carrier as claimed in claim 13, wherein the object carrier is configured as a bottom plate of a microtiter plate or of a microgrid, or is configured as a Petri dish or is configured as a microscope slide.

15. The transparent object carrier as claimed in claim 14, wherein the object carrier is flexibly configured and is configured for the cladding of cell culture flasks.

16. A process for creating a transparent object carrier for transferring light, comprising:
producing a supporting-side surface for supporting a measurement object, a rear-side surface, facing away from the supporting side, and at least three layers comprising:
an electrically insulating first layer,
a silicon-containing second layer, which contains at least 1 atomic percent silicon, arranged on the first layer, and
an electrically insulating third layer arranged on the second layer, forming an interface between the first layer and the second layer and between the second layer and the third layer,
wherein the interface between the first layer and the second layer has a first surface charge density and the interface between the second layer and the third layer has a second surface charge density,
adjusting the range and strength of the first and second surface charge densities during the production process wherein the first and second surface charge densities have the same or different signs and near-surface electrostatic forces, to form on surface sides of the object carrier, such that the electrostatic forces are embodied on both sides or on one side,
wherein the at least three layers each have a layer thickness of less than 1 RM.

17. The process as claimed in claim 16, wherein the strength of the first surface charge density is greater than the strength of the second surface charge density, or the strength of the first surface charge density is less than the strength of the second surface charge density, or the strength of the first surface charge density and the strength of the second surface charge density are equal.

18. The process as claimed in claim 16, wherein a surface charge density is from $10^{12}$ to $10^{20}$ e/cm$^2$.

19. The process as claimed in claim 16, wherein an electrically conductive layer, in particular an electrode, is formed on the supporting-side surface and/or on the rear-side surface of the transparent object carrier.

20. The process as claimed in claim 16, wherein the electrically conductive layer is configured to be transparent at least in sections, the electrically conductive layer being configured as shielding of the near-surface electrostatic forces and/or for contacting.

* * * * *